United States Patent
Bettenga et al.

(10) Patent No.: US 10,849,757 B2
(45) Date of Patent: Dec. 1, 2020

(54) SOFT ANCHOR SURGICAL FIXATION DEVICE AND METHODS OF USE THEREOF

(71) Applicant: Smith & Nephew, Inc., Memphis, TN (US)

(72) Inventors: Mason Bettenga, Memphis, TN (US); Steven Astorino, Norfolk, MA (US); Stephen M. Shepherd, Savannah, GA (US)

(73) Assignee: Smith & Nephew, Inc., Memphis, TN (US)

( * ) Notice: Subject to any disclaimer, the term of this patent is extended or adjusted under 35 U.S.C. 154(b) by 165 days.

(21) Appl. No.: 16/084,411

(22) PCT Filed: Mar. 9, 2017

(86) PCT No.: PCT/US2017/021588
§ 371 (c)(1),
(2) Date: Sep. 12, 2018

(87) PCT Pub. No.: WO2017/160589
PCT Pub. Date: Sep. 21, 2017

(65) Prior Publication Data
US 2019/0070007 A1 Mar. 7, 2019

Related U.S. Application Data

(60) Provisional application No. 62/310,185, filed on Mar. 18, 2016.

(51) Int. Cl.
*A61F 2/28* (2006.01)
*A61B 17/04* (2006.01)
*A61F 2/40* (2006.01)
*A61F 2/30* (2006.01)

(52) U.S. Cl.
CPC ........ *A61F 2/2846* (2013.01); *A61B 17/0401* (2013.01); *A61F 2/4081* (2013.01); *A61B 2017/0406* (2013.01); *A61B 2017/0409* (2013.01); *A61B 2017/0419* (2013.01); *A61F 2002/285* (2013.01); *A61F 2002/2835* (2013.01); *A61F 2002/30062* (2013.01); *A61F 2002/30461* (2013.01)

(58) Field of Classification Search
CPC ..... A61B 17/00; A61B 17/04; A61B 17/0401; A61B 17/0469; A61B 17/08; A61F 2/28; A61F 2/2846
See application file for complete search history.

(56) References Cited

U.S. PATENT DOCUMENTS

| | | | |
|---|---|---|---|
| 8,828,053 B2 * | 9/2014 | Sengun | A61B 17/0469 606/232 |
| 2012/0143215 A1 * | 6/2012 | Corrao | A61B 17/0057 606/139 |

* cited by examiner

*Primary Examiner* — Bruce E Snow
(74) *Attorney, Agent, or Firm* — Burns & Levinson, LLP; Joseph M. Maraia; Marlo Schepper Grolnic

(57) ABSTRACT

A soft anchor surgical fixation device includes two soft anchoring implants. The implants have a first elongate state where the implants may slide easily through a bone hole or tunnel, and a second axially compressed state where the implants are prevented from sliding through the bone hole or tunnel. The device also includes a suture pathway extending at least partially along and through the sidewalls of the implants. Tension on the suture transitions the implants from the first elongate state to the second compressed state.

9 Claims, 6 Drawing Sheets

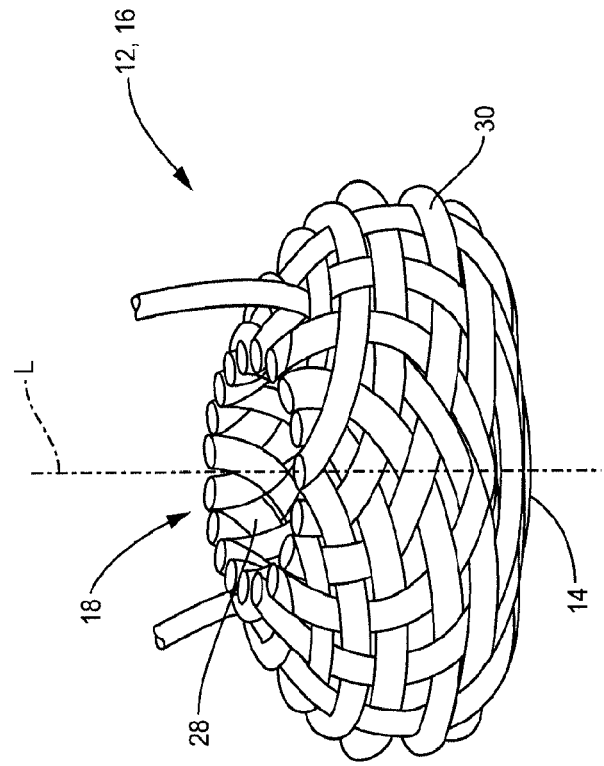
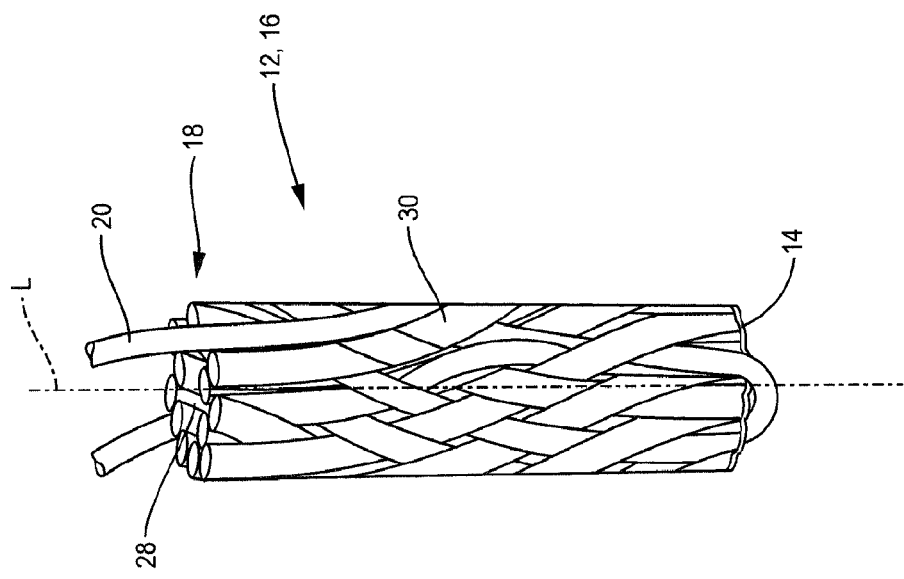

SOFT ANCHOR SURGICAL FIXATION DEVICE AND METHODS OF USE THEREOF

CROSS-REFERENCE TO RELATED APPLICATIONS

This application is the U.S. national phase entry under 35 U.S.C. § 371 of International Application No. PCT/US2017/021588, filed Mar. 9, 2017, entitled SOFT ANCHOR SURGICAL FIXATION DEVICE AND METHODS OF USE THEREOF, which in turn claims priority to and benefit of U.S. Provisional Application No. 62/310,185, filed Mar. 18, 2016, the contents of which are incorporated herein by reference in their entirety for all purposes.

FIELD

The present disclosure relates generally to a device and methods for attaching a bone graft to bone and, more particularly, to devices and methods for attaching a bone graft to a glenoid in a glenohumeral instability repair.

BACKGROUND

The shoulder joint, also referred to as the glenohumeral joint, is the joint between the glenoid cavity (a part of the scapula) and the head of the humerus (upper arm bone). The glenoid cavity is shallow, covering only about a third of the head humeral head. As a result, the glenoid cavity provides relatively little bony constraint upon motion of the humerus and the glenohumeral joint exhibits the widest range of motion of all joints in the human body. While the glenohumeral joint is also constrained by soft tissue (e.g., cartilage attached to the rim of the glenoid cavity, tendons, etc.), in general, soft tissue cannot provide the same degree of constraint as bone. Accordingly, it is relatively easy to force the humerus from its normal anatomical position with respect to the glenoid socket (i.e., dislocate the shoulder). While not life-threatening, a dislocated shoulder can cause pain and immobilization of the joint, impacting a patient's lifestyle.

In the case of severe bone loss, a surgeon may perform a "Latarjet procedure" to repair glenohumeral instability. In a Latarjet procedure, a surgeon attempts to restore bone mass to the glenoid cavity by securing a bone graft to the surface of the glenoid suffering bone loss. When successful, the bone graft acts as a scaffold, allowing the glenoid bone to grow into the bone graft and restore the lost glenoid bone mass (bone fusion). The bone graft is taken from a portion of the patient's scapula, referred to as the coracoid process or simply coracoid, with muscles still attached to the coracoid. Thus, when the coracoid graft is fused to the glenoid cavity, the muscles attached to the coracoid provide further constraint upon the glenohumeral joint. Latarjet procedures have historically provided a high success rate for repairing glenohumeral stability due to glenoid bone loss and, therefore, have become a popular course of treatment under these circumstances.

SUMMARY

Described herein is a surgical fixation device for use in a glenohumeral instability repair. The fixation device uses flexible, three-dimensional implants which may be deployed from a first, elongate, low-profile shape into a second, short, radially-expanded shape having a larger diameter than a hole or tunnel drilled through bone to perform the procedure. Advantageously, the soft anchor implants are both less expensive to manufacture than metal implants and leave no metal in the body post-procedure. Additionally, the same existing instrumentation may be used with the soft anchor implants as with traditional metal implants. While the surgical fixation device described herein is used as part of a Latarjet procedure, it is contemplated that the surgical fixation device could also be scaled for use in a patient's foot, hand, or wrist.

Further examples of the surgical fixation device and methods of use thereof may include one or more of the following, in any suitable combination.

In examples, the surgical fixation device includes a first soft anchoring implant having a first end and a second end. The first soft anchoring implant is operable to deploy from a first elongate state to a second axially compressed state. The surgical fixation device also includes a second soft anchoring implant having a first end and a second end. The second soft anchoring implant is operable to deploy from the first elongate state to the second axially compressed state. The surgical fixation device also includes a suture pathway extending between the first implant and the second implant formed by a length of suture. The suture pathway is routed through the first implant and through the second implant such that, when tension is applied to the length of suture in a first direction, one of the first and second implants deploys from the first elongate state to the second axially compressed state, and when tension is applied to the length of suture in a second direction opposite to the first direction, the other of the first and second implants deploys from the first elongate state to the second axially compressed state.

In further examples of the surgical fixation device, the first and second implants are axially aligned so that the first end the first implant and the first end of the second implant face each other, and the second end the first implant and the second end of the second implant face away from each other. When the first and second implants are in the first, elongate state, an entirety of the length of suture is slidable with respect to the suture pathway in either direction. A width or diameter of at least one of the first and second implants in the first elongate state is selected to be smaller than a width or diameter of a prepared bone hole or tunnel. A width or diameter of at least one of the first and second implants in the second axially compressed state is selected to be larger than a width or diameter of a prepared bone hole or tunnel. At least one of the first and second implants is made of one of a suture, tape, braid or mesh, and at least one of the first and second implants is made of a bioreabsorbable material. A length of at least one of the first and second implants is about 10 mm to about 30 mm, and a width or diameter of at least one of the first and second implants is about 1 mm to about 6 mm. At least one of the first and second implants has a tensile strength of about 600 N/mm2.

Examples of the method of glenohumeral instability repair of this disclosure include: forming at least one hole through a bone graft; 2) forming at least one passageway through a glenoid; 3) passing a first soft anchoring implant of a surgical fixation device through the at least one hole of the bone graft and then through the passageway of the glenoid, the first implant connected to a second soft anchoring implant by a length of suture extending therebetween, the first and second implants being operable to deploy from a first elongate state to a second axially compressed state when tension is applied to the suture; 4) positioning the second implant on a cortical side of the bone graft; 5) applying tension to the length of suture in a first direction such that the bone graft is urged into contact with the glenoid and the second implant is deployed from the first elongate state into the second axially compressed state; and 6) applying tension to the length of suture in a second direction opposite to the first direction such that the first implant is urged into contact with the posterior surface of the glenoid and is deployed from the first elongate state into the second axially compressed state. In examples, the at least one hole through the bone graft is two holes through the bone graft and the at least one passageway through the glenoid is two passageways through the glenoid. In examples, the method further includes tying a knot in the length of suture. In examples, forming the at least one passageway through the glenoid includes forming the at least one passageway from an anterior to a posterior surface of the glenoid.

Further examples of the method of glenohumeral instability repair of this disclosure include: 1) forming at least one hole through a bone graft; 2) forming at least one passageway through a glenoid; 3) passing a first soft anchoring implant of a surgical fixation device through the at least one hole of the bone graft and then through the passageway of the glenoid, the first implant coupled to a length of suture, the first implant being operable to deploy from a first elongate state to a second axially compressed state when tension is applied to the suture; 4) attaching a second soft anchor implant to the length of suture on a cortical side of the bone graft, the second implant being operable to deploy from a first elongate state to a second axially compressed state when tension is applied to the suture; 5) applying tension to the length of suture in a first direction such that the bone graft is urged into contact with the glenoid and the second implant is deployed from the first elongate state into the second axially compressed state; and 6) applying tension to the length of suture in a second direction opposite to the first direction such that the first implant is urged into contact with the posterior surface of the glenoid and is deployed from the first elongate state into the second axially compressed state.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 1A and 1B illustrate an example of a soft anchoring implant for use in the surgical fixation device of this disclosure in an elongate shape (A) and a radially-expanded shape (B);

DETAILED DESCRIPTION

Figure 2A:
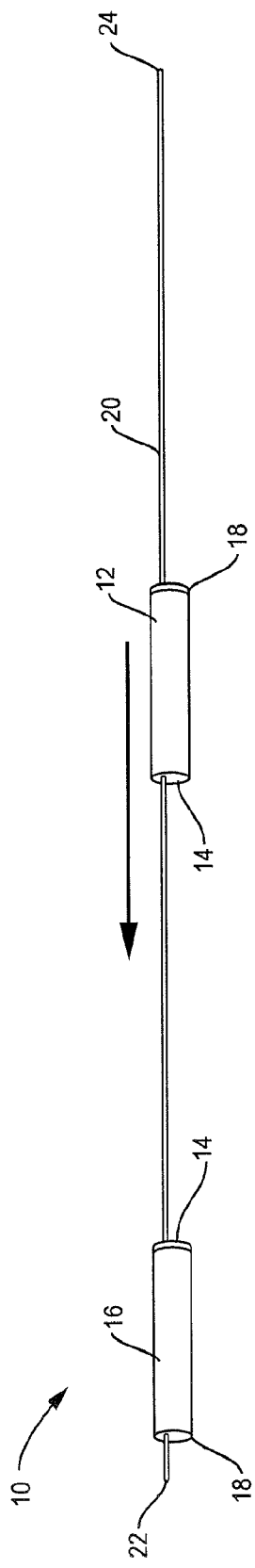
FIGS. 2A-D show an example of the suture pathway between the soft anchoring implants of the surgical fixation device.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Turning now to FIGS. 1A and 1B, the surgical fixation device 10 described herein generally includes two soft anchoring implants 12, 16 with a suture pathway routed along and through the implants 12, 16. Examples of soft anchoring implants 12, 16 may be formed from suture, tape, braid or mesh, which may be formed from a bioreabsorbable material. In FIGS. 1A and 1B, examples of implants 12, 16 are formed from a coarse, braided material 30, which may be a cylindrical, helically wound braid, such as the common biaxial braid. In examples, the implants 12, 16 may have a three-dimensional tubular shape with a closed first end 14 and either a closed or open second end 18, and a lumen 28 that is changeable in shape. Exemplary non-limiting dimensions for the implants 12, 16 are in the range of about 10 mm to about 30 mm in length, and about 1 mm to about 6 mm in width or diameter. It is also contemplated by this disclosure that one of the leading implant 12 or the trailing implant 16 is formed from a hard material, such as metal.

In FIG. 1A, the implants 12, 16 are shown in a first, pre-deployed state. Pulling the implants 12, 16 along a longitudinal axis (L) (i.e., putting the braid in tension) lengthens and narrows it. The implants 12, 16 may be pulled and manually manipulated to achieve this configuration or specialized manufacturing fixtures may be employed, such as a funnel, tube and/or pin. The length of the implants 12, 16 is gained by reducing the angle between the threads of the braided material 30 at the crossing points of the threads so that the threads align mostly parallel, which also reduces the radial distance between opposing sides and hence the overall circumference. When counter traction occurs, the opposite action occurs, and the braided material 30 longitudinally contracts axially and expands radially in a secondary, deployed state, in this case by increasing the angle between the threads (FIG. 1B). The longitudinal axis (L) is generally aligned with the insertion direction of the implants 12, 16 within bone, or aligned with a bone tunnel longitudinal axis and does not alter in orientation when in the secondary deployed state.

The braided material 30 of the soft anchoring implants 12, 16 provides an advantage in that the structure can collapse and elongate naturally due to the alignment of the threads. Other non-limiting examples of soft anchoring implants include the Q-Fix all-suture implant, manufactured by ArthroCare Corporation, Tex., USA, and is generally described in U.S. Publication No. 2013/0123810, incorporated by reference herein. Advantageously, the Q-Fix all-suture implants have a tensile strength of 600 N/mm2, six times the safety factor of typical Latarjet implants. The use of soft anchoring implants also eliminates metal or PEEK in bone, depth gaging, multiple screw sizes and the need for a screw driver. There is also no design control needed with soft anchoring implants.

The suture pathway may be routed along and through the implants 12, 16 in any configuration that causes one of the implants 12, 16 to deploy from the first elongate state to the second axially compressed state when the suture is pulled in one direction, and for the other of the implants 12, 16 to deploy from the first elongate state to the second axially compressed state when the suture is pulled in the opposite direction. FIGS. 2A-D show a non-limiting example of a suture pathway. In FIG. 2A, the leading implant 12 is located at the proximal end of the fixation device 10 and the trailing implant 16 is located at the distal end of the fixation device 10. The implants 12, 16 are configured so that the closed first ends 14 are facing each other and the open second ends 18 are facing away from each other.

Figure 2B:
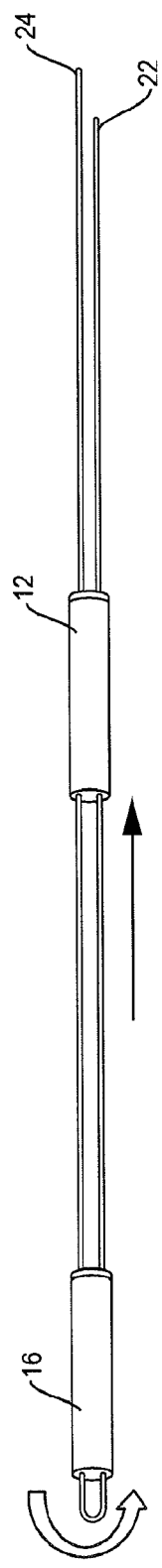
Figure 2C:
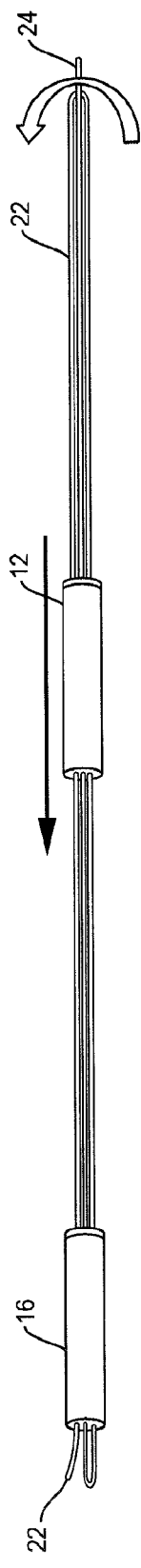
Figure 2D:
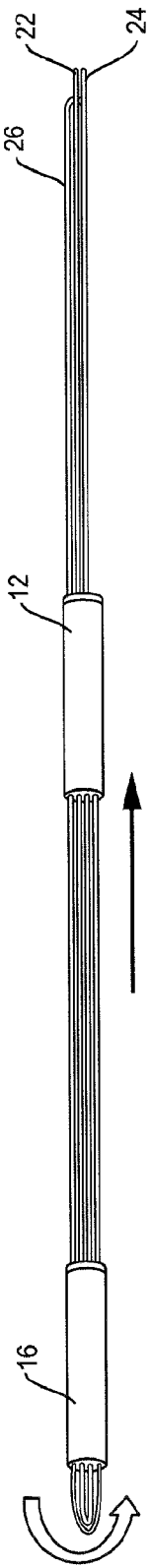

As shown in FIG. 2A, a suture 20, having a first suture end 22 and a second suture end 24, extends between the leading implant 12 and the trailing implant 16. Specifically, in FIG. 2A, the first suture end 22 is passed in a generally distal direction so as to be woven through the implants 12, 16, using a suture snare or other appropriate tool (not shown). The first suture end 22 is passed from a proximal end to a distal end of the leading implant 12 and then from a proximal end to a distal end of the trailing implant 16. Next, as shown in FIG. 2B, the first suture end 22 is looped over a portion of the distal end of trailing implant 16 and then through the implants 12, 16 in the opposite direction, i.e. from a distal end to a proximal end of trailing implant 16 and then from a distal end to a proximal end of leading implant 12. As shown in FIG. 2C, the first suture end 22 again is passed through the implants 12, 16 all the way to the distal end of trailing implant 16 and then, after looping over another portion of the distal end of trailing implant 16, returns so as to exit the proximal end of the leading implant 12 (FIG. 1D). At this point, if the suture ends 22, 24 were to be pulled in one direction, one of the implants 12, 16 would shorten in length and expand radially, as shown in FIGS. 1A and 1B. If the suture ends 22, 24 were pulled in the opposite direction, the other of the implants 12, 16 would shorten and expand.

With reference to FIGS. 3A-H, a method of glenohumeral instability repair using the surgical fixation device 10 as described above is shown generally conducted according to known procedures. A non-limiting example of such a procedure is described in International Publication No. WO 2015/191948, to Smith & Nephew, Inc., incorporated by reference herein. The method described below advantageously uses the same instrumentation as a typical method performed with metal implants.

Figure 3C:
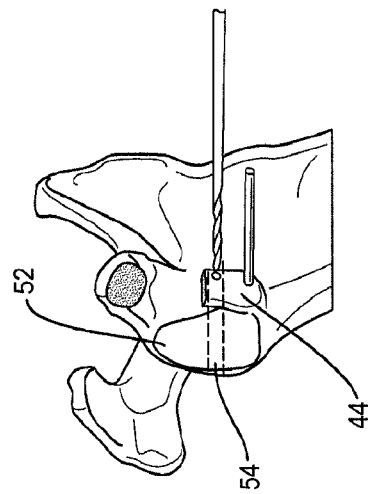
FIGS. 3A-F show a method of glenohumeral instability repair using the surgical fixation device of FIGS. 2A-D.
Figure 3B:
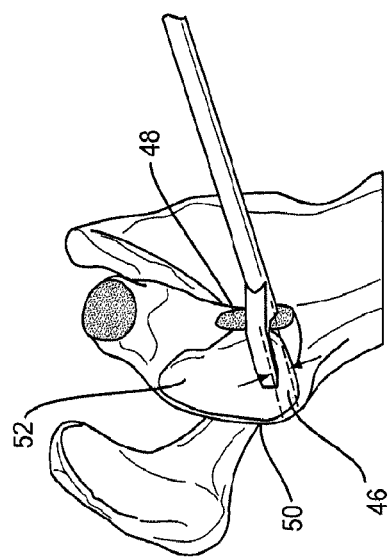
Figure 3A:
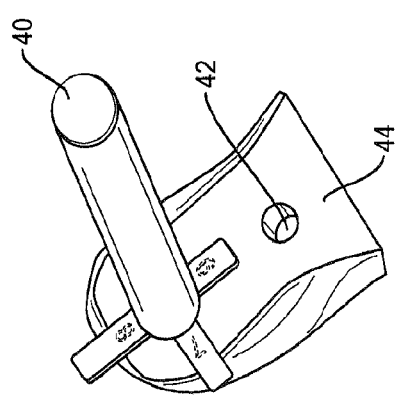

In FIG. 3A, a drill guide 40 is employed to drill at least one hole or passageway 42 at select locations within a bone graft 44. Generally, the bone graft 44 is cut with dimensions such that a surface of the bone graft 44 that contacts the glenoid is approximately 7 mm by 25 mm and such that the bone graft 44 has a height about 7 mm above the glenoid. However, the dimensions of the bone graft 44 may be adjusted in proportion to the patient's glenoid. The bone graft 44 may be prepared from the patient's bones (for example, the tricortical iliac crest) or from donor material. In a Latarjet procedure, the bone graft 44 is attached to soft tissue (not shown). In FIG. 3B, at least one tunnel 46 corresponding to the at least one hole 42 of the bone graft 44 is drilled from an anterior surface 48 to a posterior surface 50 of the glenoid 52. A width of the tunnel 46 may be about 2.8 mm. As shown in FIG. 3C, if more than one tunnel is needed, the bone graft 44 is temporarily pinned while a second tunnel 54 is drilled through the bone graft 44 and glenoid 52.

Figure 3D:
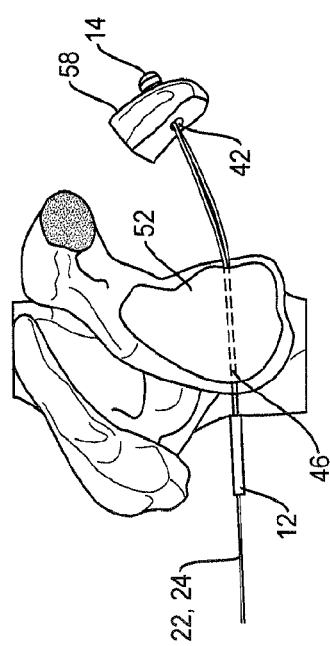
Figure 3E:
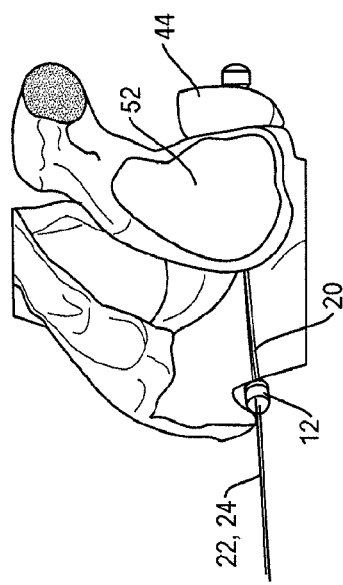
Figure 3F:
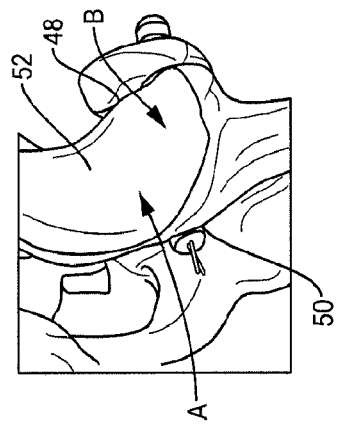

As shown in FIG. 3D, the leading implant 12, in its first elongated state, is passed through the hole 42 from the cortical side 58 of the bone graft 44 and then through the tunnel 46 of the glenoid 52 in the direction that allows the braided material 30 (FIG. 2A) of the leading implant 12 to remain in an undeployed state. The suture ends 22, 24 are pulled in one direction so that the trailing implant 14 expands and is secured on the cortical side 58 the bone graft 44 in its secondary, deployed state, with a diameter larger than a diameter of the hole 42 of the bone graft 44. In FIGS. 3E and 3F, pulling on the suture ends 22, 24 in the opposite direction causes the leading implant 12 to deploy and move toward the glenoid 52 until it is secured against the posterior surface 50 of the glenoid 52, with a diameter larger than a diameter of the tunnel 46 of the glenoid 52. The tension in the suture 20 causes the leading implant 12 to apply pressure in a first direction (A) to the posterior surface 50 of the glenoid 52 and the trailing implant 14 to apply pressure in an opposite direction (B) to the bone graft 44, such that the bone graft 44 is compressed against the glenoid 52. The pressure created by the surgical fixation device 10 between the bone graft 44 and the anterior surface of the glenoid 52 will cause the two bones to fuse during the healing process.

Figure 3H:
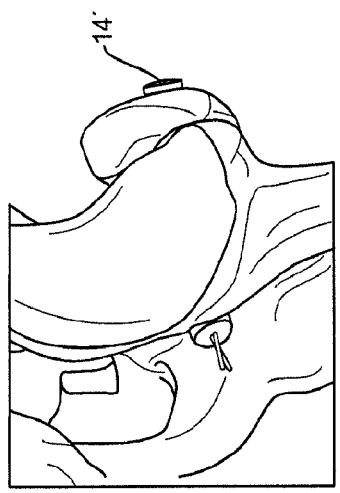
FIGS. 3G and 3H show an alternative method of glenohumeral instability repair using a soft anchoring implant and a hard metal implant.
Figure 3G:
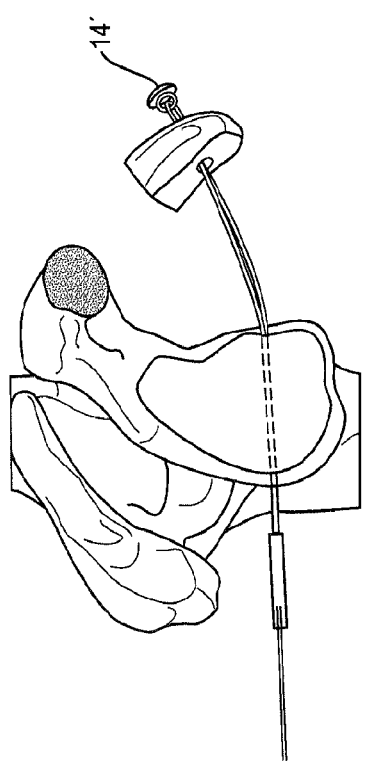
Figure 4:
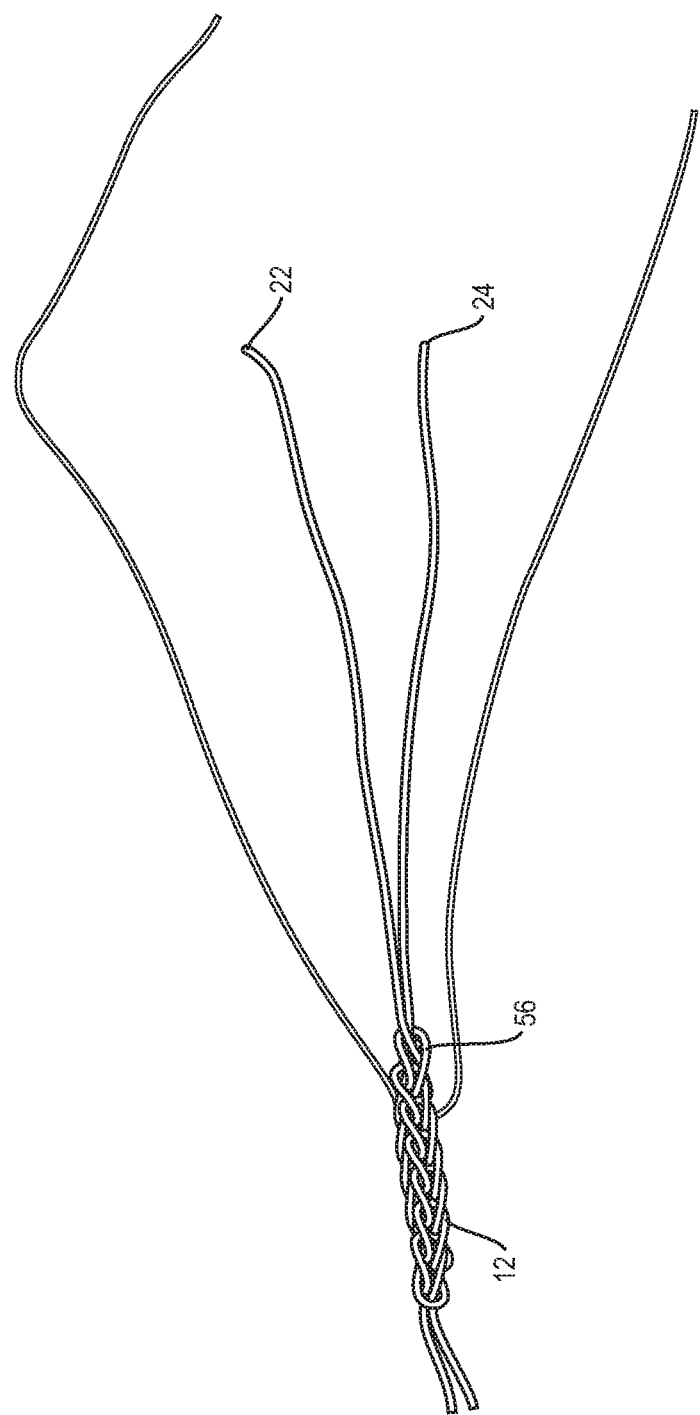
FIG. 4 shows a surgical knot tied in the surgical fixation device of this disclosure.

FIGS. 3G and 3H show an alternative example of the method where the trailing implant 14' is a metal button. Additionally, in an example shown in FIG. 4, a surgical knot 56, such as a nice knot, may be tied in the suture ends 22, 24 after the leading implant 12 has been secured to the glenoid 52 (not shown).

There are number of possible variations to the Latarjet procedure described above with regard to FIGS. 3A-3F. For example, the surgical fixation device 10 may be installed from the opposite direction. In particular, leading implant 12 may be passed through the tunnel 46 in the reverse direction as described above with regard to FIGS. 3A-3F, i.e., from the posterior surface 50 of the glenoid 52 to the cortical side 58 of the bone graft 44. The implants 12, 14 are deployed and the suture 20 tensioned as described above with regard to FIGS. 3A-3F.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

The invention claimed is:
1. A surgical fixation device comprising:
   a first soft anchoring implant having a first end and a second end, the first soft anchoring implant operable to deploy from a first elongate state to a second axially compressed state;
   a second soft anchoring implant having a first end and a second end, the second soft anchoring implant operable to deploy from the first elongate state to the second axially compressed state; and a suture pathway extending between the first implant and the second implant formed by a length of suture, the suture pathway comprising:
- a first suture end and a second suture end, the second suture end extending from the second end of the first soft anchoring implant, the first suture end woven a first time from the second end to the first end of the first soft anchoring implant, and then woven a first time through from the first end to the second end of the second soft anchoring implant, and then looped a first time over the second end of the second soft anchoring implant, and then woven a first time from the second end to the first end of the second soft anchoring implant, and then woven a first time from the first end to the second end of the first soft anchoring implant, such that the first suture end extends from the second end of the first soft anchoring implant adjacent the second suture end; and
- the first suture end woven a second time from the second end to the first end of the first soft anchoring implant, and then woven a second time through from the first end to the second end of the second soft anchoring implant, and then looped a second time over the second end of the second soft anchoring implant, and then woven a second time from the second end to the first end of the second soft anchoring implant, and then woven a second time from the first end to the second end of the first soft anchoring implant, such that the first suture end extends from the second end of the first soft anchoring implant adjacent the second suture end.

2. The surgical fixation device of claim 1, wherein, when the first and second soft anchoring implants are in the first, elongate state, an entirety of the length of suture is slidable with respect to the suture pathway in either direction.

3. The surgical fixation device of claim 1, wherein a width or diameter of at least one of the first and second soft anchoring implants in the first elongate state is selected to be smaller than a width or diameter of a prepared bone hole or tunnel.

4. The surgical fixation device of claim 1, wherein a width or diameter of at least one of the first and second soft anchoring implants in the second axially compressed state is selected to be larger than a width or diameter of a prepared bone hole or tunnel.

5. The surgical fixation device of claim 1, wherein at least one of the first and second soft anchoring implants comprises one of a suture, tape, braid or mesh.

6. The surgical fixation device of claim 1, wherein at least one of the first and second soft anchoring implants comprises a bioreabsorbable material.

7. The surgical fixation device of claim 1, wherein a length of at least one of the first and second soft anchoring implants is about 10 mm to about 30 mm.

8. The surgical fixation device of claim 1, wherein a width or diameter of at least one of the first and second soft anchoring implants is about 1 mm to about 6 mm.

9. The surgical fixation device of claim 1, wherein at least one of the first and second soft anchoring implants has a tensile strength of about 600 N/mm2.

* * * * *